(12) United States Patent
Cadwalader et al.

(10) Patent No.: US 7,767,990 B2
(45) Date of Patent: Aug. 3, 2010

(54) RADIATION ATTENUATION SYSTEM FOR LATERAL IMAGING

(75) Inventors: John A. Cadwalader, Overland Park, KS (US); William W. Orrison, Las Vegas, NV (US)

(73) Assignee: Worldwide Innovations & Technologies, Inc., Overland Park, KS (US)

( * ) Notice: Subject to any disclaimer, the term of this patent is extended or adjusted under 35 U.S.C. 154(b) by 318 days.

(21) Appl. No.: 11/621,438

(22) Filed: Jan. 9, 2007

(65) Prior Publication Data

US 2008/0164425 A1  Jul. 10, 2008

(51) Int. Cl.
*G21F 3/02* (2006.01)

(52) U.S. Cl. ............... 250/519.1; 250/505.1; 250/515.1; 250/516.1; 378/203; 128/846; 128/849; 128/853; 128/854; 128/855

(58) Field of Classification Search ............... 250/505.1, 250/515.1, 516.1, 519.1; 378/203; 128/846, 128/849, 853, 854, 855, 856
See application file for complete search history.

(56) References Cited

U.S. PATENT DOCUMENTS

| | | | | |
|---|---|---|---|---|
| 2,794,128 A | * | 5/1957 | Shasky | 250/519.1 |
| 5,038,047 A | * | 8/1991 | Still | 250/516.1 |
| 5,417,225 A | * | 5/1995 | Rubenstein et al. | 128/849 |
| 6,325,538 B1 | * | 12/2001 | Heesch | 378/203 |
| 6,653,648 B2 | * | 11/2003 | Goldstein | 250/515.1 |
| 6,674,087 B2 | * | 1/2004 | Cadwalader et al. | 250/515.1 |
| 2003/0102463 A1 | | 6/2003 | Smith | |
| 2004/0041107 A1 | * | 3/2004 | Cadwalader et al. | 250/519.1 |
| 2005/0213712 A1 | * | 9/2005 | Cadwalader et al. | 378/203 |
| 2006/0251219 A1 | * | 11/2006 | Cadwalader et al. | 378/203 |

OTHER PUBLICATIONS

International Search Report and Written Opinion for International Application No. PCT/US2008/050486, mail date Jul. 2, 2008, 7 pages.

* cited by examiner

*Primary Examiner*—Robert Kim
*Assistant Examiner*—Michael Maskell
(74) *Attorney, Agent, or Firm*—Foley & Lardner LLP

(57) ABSTRACT

A radiation attenuation system for attenuating radiation during lateral radiographic imaging of an object is provided. The system includes a first radiation attenuating barrier that is substantially conformable to the object and configured to at least partially cover the object. The first radiation attenuating barrier has a fenestration area defining at least one opening. The system further includes a second radiation attenuating barrier coupled to the first radiation attenuation barrier. The second radiation attenuating barrier is selectively movable between a collapsed position and a generally upright position relative to the first radiation attenuating member.

20 Claims, 11 Drawing Sheets

RADIATION ATTENUATION SYSTEM FOR LATERAL IMAGING

BACKGROUND

The present description relates generally to systems for and methods of attenuating radiation during radiographic imaging of an object. More particularly, the present description relates to systems for and methods of shielding the object and/or persons near the object from primary and/or secondary radiation during lateral radiographic imaging of the object of a type utilized during kyphoplasty and vertebroplasty procedures, among others.

Lateral radiographic imaging refers to radiographic imaging wherein radiation is emitted at a lateral side of an object (e.g., a patient, etc.) and directed through an opposite lateral side of the object for purposes of generating an internal image of the object. Often, in lateral radiographic imaging, the primary radiation beam is emitted in a direction that is relatively horizontal and substantially parallel to a ground surface or a support surface for the object. Such an imaging technique is distinct from the more common imaging technique of emitting radiation into either the front or back of the object and directing it through the other of the front or back of the object in a vertical direction that is substantially perpendicular to the ground surface or the support surface for the object. Several medical procedures utilize lateral radiographic imaging of a patient to visualize and/or monitor the procedure. An example of such a medical procedure is vertebroplasty, sometimes referred to as percutaneous vertebroplasty.

Percutaneous vertebroplasty involves the injection of a bone cement or other suitable biomaterial into a vertebral body via a percutaneous route under radiographic imaging guidance (e.g., fluoroscopy, Computed Tomography, etc.). The cement is injected as a semi-liquid substance through a delivery device (e.g., needle, syringe, cannula, etc.) that has been passed into the vertebral body, generally along a transpedicular or posterolateral approach. Percutaneous vertebroplasty is intended to provide structural reinforcement of a vertebral body through injection, by a minimally invasive percutaneous approach, of bone cement into the vertebral body. Percutaneous vertebroplasty can result in increased structural integrity, decreased micromotion at the fracture site and possibly a destruction of pain fibres due to the heat of the bone cement as it polymerizes and sets.

Generally, when performing vertebroplasty, the delivery device is passed down the pedicle until it enters the vertebral body and reaches the junction of the anterior and middle thirds. The delivery device must be inserted at a suitable angle and pass through the periosteum, down the pedicle and into the vertebral body. A suitable cement is prepared and injected through the delivery device and into the vertebral body. Guidance of the delivery device and monitoring of the cement injection is provided via a lateral radiographic imaging technique, such as fluoroscopy. The injection is stopped as the cement starts to extend into some unwanted location such as the disc space or towards the posterior quarter of the vertebral body, where the risk of epidural venous filling and hence spinal cord compression is greatest. The injection is also discontinued if adequate vertebral filling is achieved.

During a vertebroplasty procedure, medical personnel (e.g., technicians, assistants, nurses, physicians, surgeons, etc.) are often positioned near the patient undergoing the procedure. For example, the procedure usually requires someone (typically the physician) to hold the delivery device in position. This is normally required since the delivery device should be stabilized and oriented in the desired position in order for the intended target to be reached. As such, someone is likely to be positioned near the patient as the patient during the procedure.

Medical personnel positioned near the patient during a vertebroplasty procedure are susceptible to radiation since the patient is being irradiated so that the procedure can be monitored. Specifically, medical personnel positioned near the patient are susceptible to exposure to primary beam radiation and scatter radiation. Scatter radiation is a secondary radiation generated when the primary radiation interacts with the object being impinged. Scatter radiation has a frequency range lower than the primary radiation beam and generally moves in a variety of uncontrollable directions. Scatter radiation, like primary radiation, can cause damage to living tissue. The amount of scatter radiation present during a vertebroplasty procedure is increased since the radiographic image is being taken in a lateral (e.g., horizontal relative to a support surface of the patient table, partially lateral or oblique relative to the support surface, etc.) and the primary radiation beam is likely to scatter after impinging a lateral side of the patient, the patient table and/or walls or other objects within the procedure room. As such, known radiation attenuating safeguards, such as table drapes or standard patient shields used during more common radiographic imaging techniques, may not provide the medical personnel with a desired level of protection from the scatter radiation. This issue of scatter radiation is not limited to vertebroplasty procedures, as it becomes an issue for any procedure utilizing lateral radiographic imaging.

Thus, there is a need for a radiation attenuation system for and method of shielding an object from primary beam radiation during lateral radiographic imaging of the object. There is also a need for a radiation attenuation system that is configured to shield persons positioned near an object undergoing lateral radiographic imaging from primary beam radiation. There is further a need for a radiation attenuation system that is configured to shield an object or persons positioned near the object undergoing lateral radiographic imaging from scatter radiation. Yet further, there is a need for a radiation attenuation system that is multifunctional so that it can be used effectively with more common radiographic imaging techniques and can also be used effectively with lateral imaging techniques. There is further a need for a radiation attenuation system that is reconfigurable (e.g., positionable, collapsible, adaptable, etc.) so that it can be effectively used in various applications and/or so that it can adapt to changing conditions that may occur during a procedure. There is also a need for a radiation attenuation system that can be easily shipped and/or stored. There is further a need for a radiation attenuation system having a configuration that may reduce the tension or stress experienced by a patient during a radiological procedure. There is further a need for radiation attenuation system addressing these and/or any other need.

SUMMARY

One exemplary embodiment relates to a radiation attenuation system for attenuating radiation during lateral radiographic imaging of an object. The system includes a first radiation attenuating barrier that is substantially conformable to the object and configured to at least partially cover the object. The first radiation attenuating barrier has a fenestration area defining at least one opening. The system further includes a second radiation attenuating barrier coupled to the first radiation attenuation barrier. The second radiation attenuating barrier is selectively movable between a collapsed position and a generally upright position relative to the first radiation attenuating member.

Another exemplary embodiment relates to a shield for attenuating radiation during lateral radiographic imaging of a patient. The shield includes a drape formed of a first radiation attenuating material and substantially conformable to the patient. The drape is configured to at least partially cover a non-target area on the patient. The shield also includes a flap formed of a second radiation attenuating material and coupled to the drape. The flap is supported at a generally upright position relative to the drape. The flap is configured to attenuate scatter radiation during lateral radiographic imaging of the patient.

Another exemplary embodiment relates to a method of attenuating radiation during lateral radiographic imaging of a patient. The method includes the step of providing a radiographic device configured to emit a primary radiation beam at a first lateral side of the patient towards a second lateral side of the patient in a direction that is substantially perpendicular to a longitudinal axis of the patient. The method also includes the steps of positioning a first radiation shield at least partially over a non-target area on the patient, aligning a fenestration area of the first radiation shield with a target area on the patient, positioning a second radiation shield at an orientation that is substantially upright relative to the first radiation shield. The first radiation shield is substantially conformable to the patient. The second radiation shield is coupled to the first radiation shield and configured to attenuate scatter radiation during lateral radiographic imaging of the patient.

DETAILED DESCRIPTION

Figure 1:
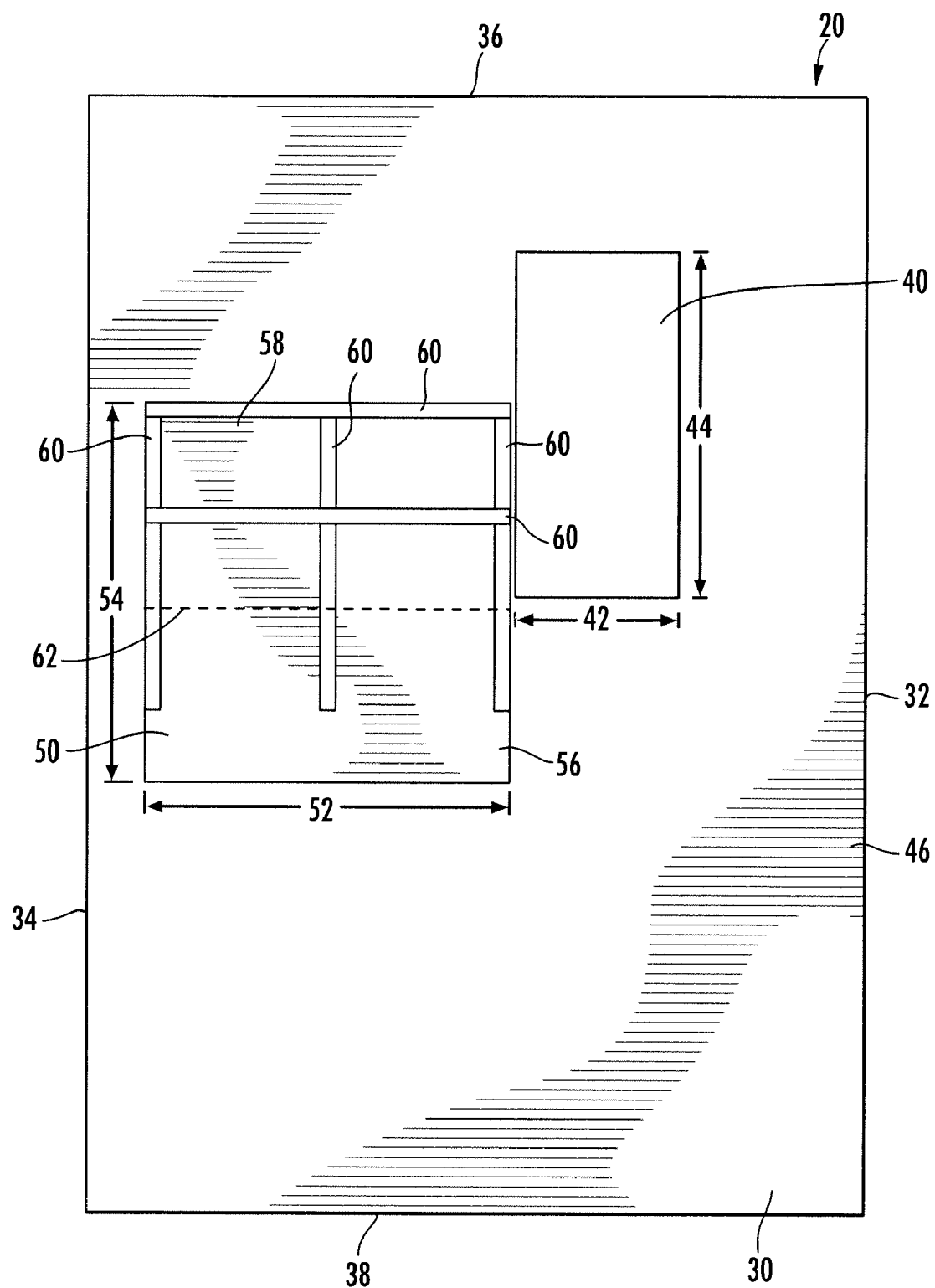
FIG. 1 is a top planar view of a radiation attenuation system according to an exemplary embodiment.

Referring to FIGS. 1 through 11, a radiation attenuation system 20 and components thereof are shown according to exemplary embodiments. Generally, radiation attenuation system 20 includes one or more radiation shields or barriers supported in a manner and at a position that may be useful in attenuating (e.g., blocking, reflecting, absorbing, etc.) primary beam radiation and/or secondary or scatter radiation generated during lateral radiographic imaging of an object (e.g., patient, etc.). For purposes of the present disclosure, the phrase "lateral radiographic imaging," unless expressly stated otherwise, is used broadly to refer to not only literal lateral imaging of an object (i.e., side-to-side wherein the primary radiation beam is emitted in a horizontal direction that is substantially parallel to a ground surface or a support surface for the object), but also partially lateral or oblique imaging of the object (i.e., wherein the primary radiation beam is emitted at an angle (e.g., 20, 30 or 40 degrees, etc.) relative to a ground surface or a support surface for the object).

Radiation attenuation system 20 generally includes a first radiation shield or barrier provided in the form of a cover or drape and a second radiation barrier provided in the form of a supplemental member or flap coupled to the first radiation barrier and extending upwardly from the first radiation barrier.

It should be noted that for purposes of this disclosure, the term "coupled" is used broadly to mean the joining or combining of two or more members (e.g., portions, layers, materials, components, etc.) directly or indirectly to one another. Such joining or combining may be relatively stationary (e.g., fixed, etc.) in nature or movable (e.g., adjustable, etc.) in nature. Such joining or combining may be achieved with the two members or the two members and any additional intermediate members being integrally formed as a single unitary body with one another (e.g., one-piece, etc.) or with the two members or the two members and any additional intermediate member being attached to one another. Such joining or combining may be intended to be relatively permanent in nature or alternatively may be intended to be relatively detachable or removable in nature.

The first radiation barrier is configured to at least partially cover an area of a patient during a procedure (e.g., a non-target area, etc.), and is intended to protect the patient from unnecessary radiation exposure (both primary beam radiation and scatter radiation) during the procedure. In addition to protecting the patient, the first radiation barrier may also be useful in protecting one or more individuals present during the procedure (e.g., technicians, assistants, nurses, physicians, surgeons, etc.), referred to generally herein as medical personnel. Medical personnel present during the radiographic imaging of the patient may also be susceptible to radiation exposure from the primary radiation beam (e.g., during a fluoroscopy procedure, etc.), but are more likely to be susceptible to radiation exposure from secondary or incidental scatter radiation. The first radiation barrier protects against scatter radiation by absorbing at least a portion of the primary radiation beam and scatter radiation.

The first radiation barrier includes a fenestration area which provides medical personnel (typical a physician) with access to an area of interest on the patient (e.g., target area, etc.) through an aperture or opening. During a procedure, a radiographic visualization or imaging device (e.g., fluoroscope, etc.) will likely be positioned such that a radiation emitter of the device is located at a first lateral side of the patient and a corresponding radiation receiver of the device is located at an opposite second lateral side with the fenestration area of the first radiation barrier provided therebetween. One or more medical personnel are likely to be positioned near the patient and, in particular, near the fenestration area during the procedure, and as such, are likely to be positioned in the path of, or closely adjacent to, the primary radiation beam (i.e., between the emitter and receiver) and/or an area likely to be exposed by scatter radiation.

To provide further protection against radiation for the patient and/or medical personnel, the second radiation barrier is provided. The second radiation barrier is provided near the fenestration area and extends upwardly from the first radiation barrier. For example, the second radiation barrier may extend upwardly in a direction that is substantially perpendicular to the first radiation barrier and laterally across at least a portion of the first radiation barrier in a direction that is substantially parallel with the primary radiation beam originating at the radiation emitter of the radiographic imaging device. In such a position, the second radiation barrier is positioned between the medical personnel attending to the fenestration area and the primary radiation beam (and/or scatter radiation).

Figure 2:
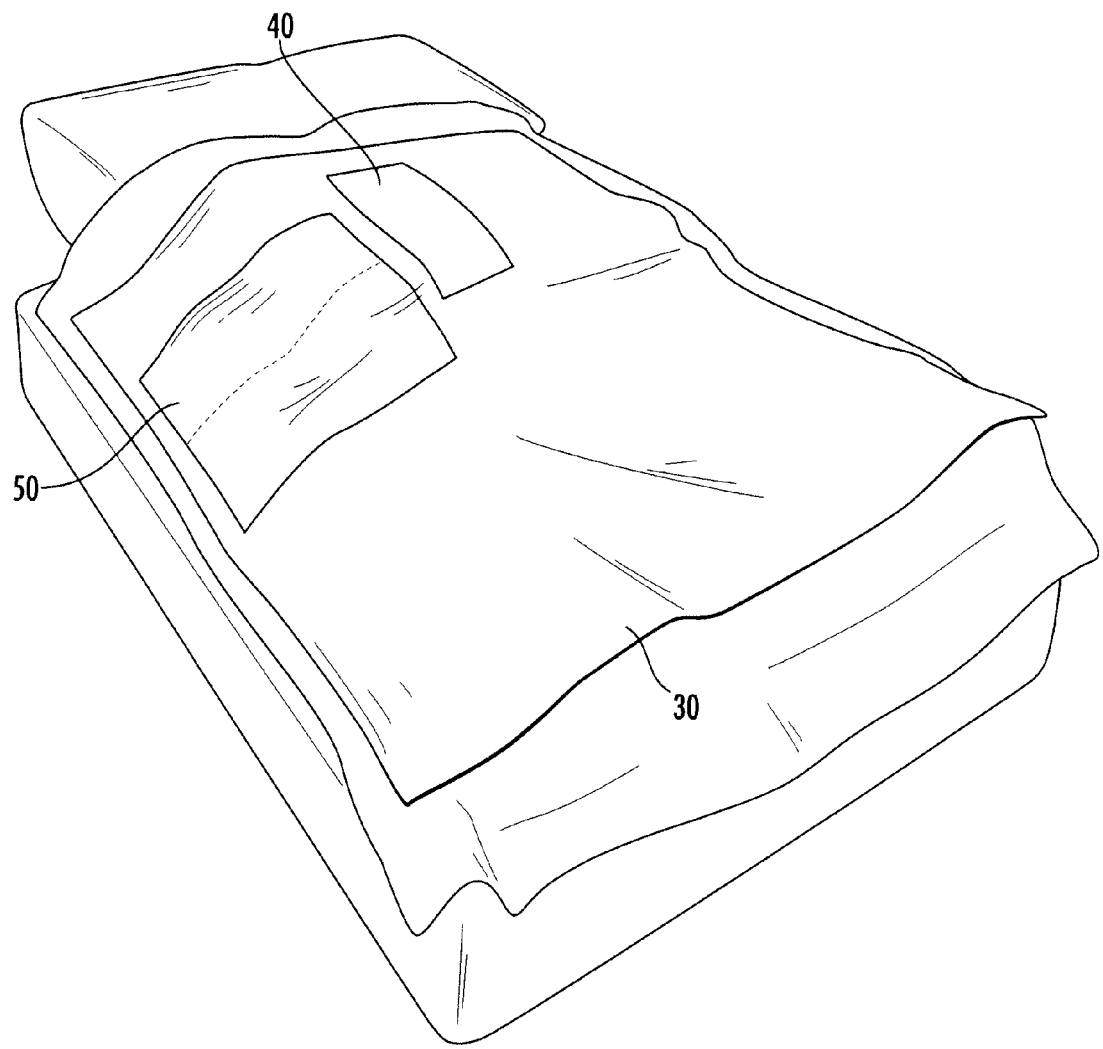
FIG. 2 is a perspective view of the radiation attenuation system of FIG. 1 shown in a retracted position.
Figure 3:
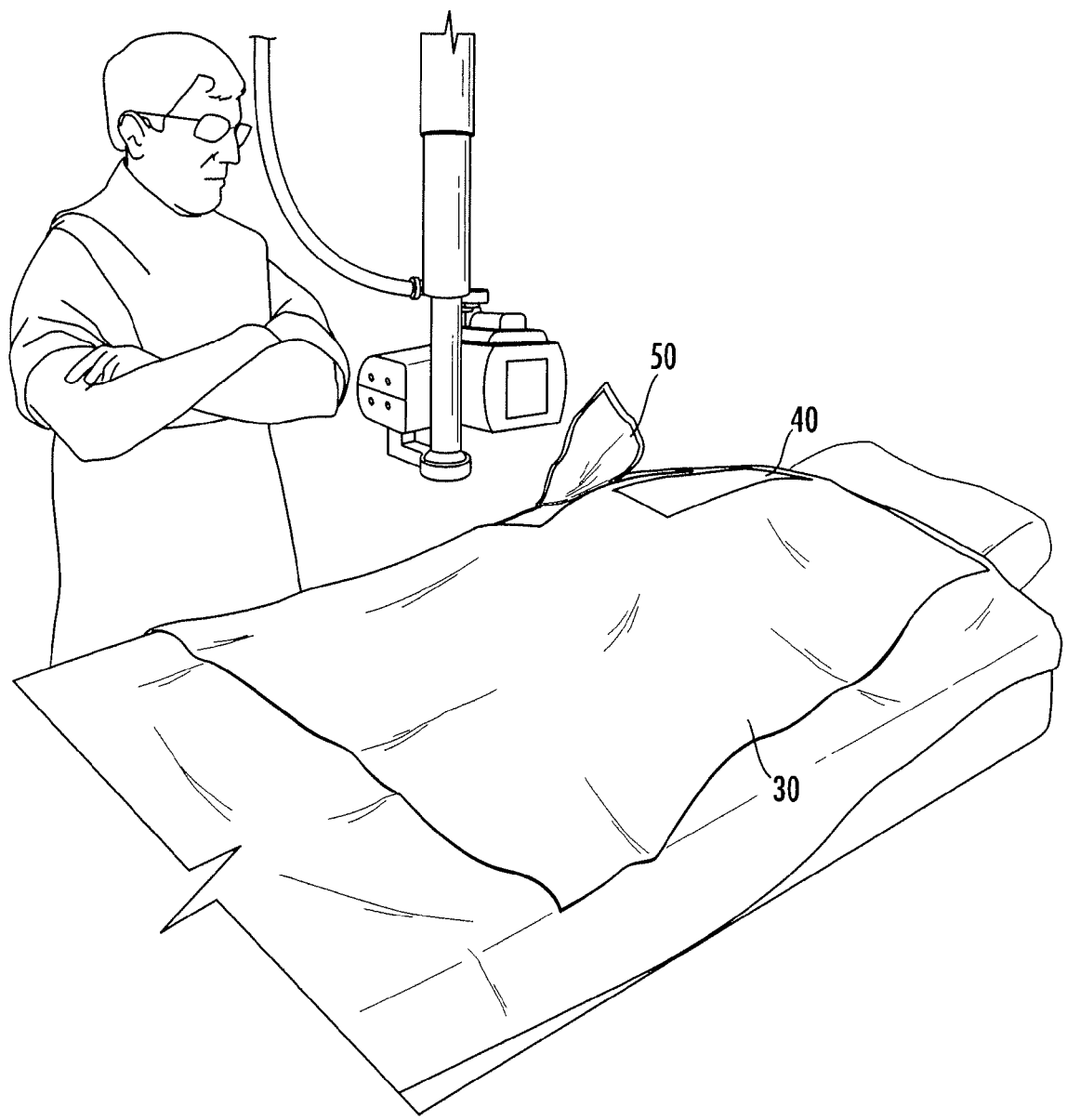
FIG. 3 is a perspective view of the radiation attenuation system of FIG. 1 shown in an extended position.

According to an exemplary embodiment, the second radiation barrier is selectively movable (e.g., reconfigurable, adjustable, repositionable, formable, etc.) between a first position (e.g., stowed position, retracted position, collapsed position, flattened position, etc.) and a second position (e.g., use position, upright position, attenuating position, etc.). An example of the first position is shown in FIG. 1, while an example of the second position is shown in FIG. 2. In the first or non-extended position, the second radiation barrier is shown as overlapping a portion of the first radiation barrier and orientated substantially parallel thereto. Such positioning of the second radiation barrier may be useful for shipping and/or storing of radiation attenuation system 20. Such positioning may also allow the radiation attenuation system 20 to be used as a more conventional patient drape or shield (e.g., during a non-lateral radiographic imaging technique, etc.).

Configuring the second radiation barrier as a selectively movable member may advantageously provide medical personnel with flexibility during the procedure. For example, while it may be beneficial to use the second radiation barrier throughout a procedure, at certain times the second radiation barrier may interfere with one or more medical personnel and/or for various reasons become unneeded. Further, it may be desirable to change the orientation and/or positioning of the second radiation barrier in the extended position to precisely position it response to the position of the medical personnel. By providing a second radiation barrier that is selectively movable, medical personnel can control when the second radiation barrier is used and, if used, the position of it during use (e.g., height, angle, etc.). The second radiation barrier is also self-supportive in the extended position, meaning that medical personnel does not have to hold the second radiation barrier in the desired position in order to retain it in this position. As detailed below, the second radiation barrier may be supported by a support structure fixedly coupled between the first radiation barrier and the second radiation barrier (e.g., one or more adjustable bands, etc.), by a support structure removably coupled to the second radiation barrier (e.g., an L-shaped bracket, etc.), or by any other suitable support technique. The "self-supportive" feature may advantageously allow the medical personnel to conduct other tasks during the procedure and/or may eliminate the number medical personnel required around the patient.

It should be noted that while the exemplary embodiments are described and illustrated herein as a radiation attenuation system for shielding medical personnel (and possibly the patient) during lateral radiographic imaging of the patient, the radiation attenuation system may be configured to shield medical personnel (and possibly the patient) during any radiological procedure. For example, radiation attenuation system 20 is suitable for use with diagnostic procedures (i.e., procedures allowing non-invasive examination or investigation of a patient such as x-ray examinations, Computed Tomography scanning procedures, or the like), therapeutic procedures (i.e., procedures wherein anatomical regions of a patient are irradiated as a treatment), and/or various invasive procedures in addition to those mentioned herein.

Also, radiation attenuation system 20 may be used regardless of the position of the patient. For example, the patient may be provided in a supine position wherein the patient is positioned on his or her back with the legs of the patient being straight or bent, a prone position wherein the patient is positioned face down, and/or a lateral position wherein the patient is positioned on one side. With a patient in the lateral position, lateral radiological imaging of the patient, as that phrase is defined herein, would involve emitting the primary radiation beam towards the front or back of the patient. Further still, radiation attenuation system 20 is suitable for use with procedures other than kyphoplasty and vertebroplasty, wherein lateral radiographic imaging is utilized for visualization and/or monitoring of the procedure. For example, radiation attenuation system 20 may be used during various pain management procedures (such as spinal procedures) and can be used during any procedure wherein it would be beneficial to use a radiation attenuation system having a selectively movable flap.

FIG. 1 is a top planar view showing radiation attenuation system 20 according to an exemplary embodiment and in a relatively flattened or non-extended position. Radiation attenuation system 20 generally comprises a first radiation shield (e.g., primary barrier, patient shield, cover, blanket, etc.), shown as a drape 30, and a second radiation shield (e.g., scatter radiation barrier, supplemental member, etc.), shown as a flap 50, coupled to drape 30.

Drape 30 is shown in the form of a rectangular or rectilinear member configured to be placed over an area of a patient undergoing the procedure or otherwise susceptible to unnecessary radiation exposure (e.g., a non-target area, etc.). Drape 30 is defined by a first lateral side edge, shown as a right edge 32, a second lateral side edge, shown as a left edge 34, an upper lateral edge, shown as a top edge 36, and a lower lateral edge, shown as a bottom edge 38. Right edge 32, left edge 34, top edge 36 and bottom edge 38 are all shown as continuous linear edges, but alternatively, may be curvilinear edges or discontinuous edges having both linear and curvilinear portions. For example, drape 30 may be contoured to conform to various portions of a patient and/or to better drape over a patient in the areas for which shielding is sought. By way of example only, top edge 36 may include a curvilinear cutout portion configured to receive the neck of a patient when drape 30 is positioned over the patient.

The size, shape, and configuration of drape 30 may be provided in any number of forms depending on various design criteria such as type of procedure, typical size of patient, type of radiographic imaging device being used, etc. Drape 30 could be of sufficient width and length to span entirely across the patient and a patient table, or alternatively could be configured only span across a portion of the patient. According to an exemplar embodiment, drape 30 is sized to cover a substantial portion of the patient, with top edge 36 intended to be positioned near the head of the patient, bottom edge 38 intended to be positioned near the feet of the patient, right edge 32 intended to drape over the left side of the patient, and left edge 34 intended to drape over the right side of the patient. Drape 30 is characterized by an ability to attenuate radiation while possessing the ability to be relatively lightweight and highly conformable to the patient.

Drape 30 includes one or more radiation attenuating members (e.g., sheets, films, pads, inserts, etc.) made of a radiation attenuating material. These radiation attenuating members may span across the entire drape 30, or alternatively, may be provided in certain key areas on drape 30 (e.g., areas likely to cover non-target areas on the patient that are susceptible to radiation exposure, etc.). According to an exemplary embodiment, the radiation attenuating material is generally light and flexible to maximize workability for bending, folding, reconfiguring, etc., or otherwise manipulating drape 30. The attenuating material may be formable (e.g., deformable) or compliant, and/or relatively "stretchable" (e.g., elastic). According to alternative embodiments, the attenuating material used may be generally rigid and inflexible, and/or substantially weighted.

According to an exemplary embodiment, the compliant nature of the radiation attenuating member allows drape 30 to reside closely next to the body of the patient. Drape 30 is comfortable and fits positively against the undulating surface of the patient thus improving its stability during the procedure. The coefficient of friction between drape 30 and the surface of the patient may add to that stability, preventing movement of drape 30 during the procedure and further obviating the need to take extraordinary measures to prevent slippage or movement of drape 30.

The radiation attenuating member may be fabricated of any radiation attenuation material including, but not limited to, bismuth, barium, lead, tungsten, antimony, copper tin, aluminum, iron, iodine, cadmium, mercury, silver, nickel, zinc, thallium, tantalum, tellurium, and uranium. Anyone of the aforementioned radiation attenuation materials alone or in a combination of two or more of the radiation attenuation materials may provide the desired level of radiation attenuation. According to an exemplary embodiment, the radiation attenuating material is comprised of a polymeric matrix charged with an attenuating filler. Examples of suitable radiation attenuation materials are disclosed in U.S. Pat. No. 4,938,233, entitled "Radiation Shield," and U.S. Pat. No. 6,674,087, entitled "Radiation Attenuation System," both of which are hereby incorporated by reference in their entirety. It should be noted that the radiation attenuating member is not limited to such radiation attenuating materials, and according to the various alternative embodiments, may be formed of any suitable radiation attenuating material including more conventional attenuating materials (e.g., lead-based materials, etc.).

The radiation transmission attenuation factor of the radiation attenuating member may vary depending upon the intended application of radiation attenuation system 20 and/or the number of layers of the attenuating members is provided. According to one exemplary embodiment, the radiation attenuating member has a radiation transmission attenuation factor of a percent (%) greater than about 50%, suitably greater than about 75%, suitably greater than about 90%, suitably greater than about 95% (with reference to a 90 kVp x-ray beam). According to various alternative embodiments, radiation attenuating member may have a radiation transmission attenuation factor of a percent less that 50% such as 10-50% or 10-20%. The radiation attenuating member may also at least partially attenuate gamma rays, and may have a gamma ray attenuation factor of at least 10% of a 140 keV gamma radiation source.

Referring further to FIG. 1, drape 30 is further shown as including a fenestration area defined by one or more apertures (e.g., slits, missing portions, keyway, cut-out, etc.), shown as an opening 40. Opening 40 provides an entry point to an area of interest on the patient (e.g., target area, etc.) for conducting various invasive procedures, such as fluoroscopic guidance and/or manipulation of instruments during exploratory or surgical procedures. According to an exemplary embodiment, opening 40 is located at a position on drape 30 that provides medical personnel with relatively unobstructed access to the spine of a patient. Such positioning of opening 40 may be useful during a variety of spinal procedures such as a vertebroplasty procedure. In such an example, opening 40 is sized to receive a delivery device used in the vertebroplasty procedure to deliver cement to a vertebral body.

Opening 40 of the fenestration area is shown as being a rectangular opening having a width 42 that is between approximately 2 inches and approximately 8 inches and a length 44 that is between approximately 4 inches and approximately 18 inches. According to one exemplary embodiment, opening 40 has a width 42 of approximately 4 inches and a length 44 of approximately 9 inches. According to the various exemplary embodiments, opening 40 may have any of a variety of shapes (e.g., circular, triangular, non-uniform, square, etc.) provided in any of a number of sizes. For example, opening 40 may be tapered at one or more ends to further limit the amount of the patient that is exposed to radiation.

Drape 30 further includes a covering 46 disposed about or containing the radiation attenuating member. Covering 46 may enhance processability, provide softness or comfort to a patient, and/or may allow radiation attenuation system 20 to be more easily cleaned and/or sanitized. Covering 46 is preferably made of a fabric material such as that of a surgical drape, but can also be made of a non-fabric material such as a plastic sheet, non-woven paper material, or any other material suitable for covering the radiation attenuating member. According to an exemplary embodiment, covering 46 is constructed from a front sheet and a back sheet which are coupled together at the periphery to enclose the radiation attenuating member.

Covering 46 may be configured so that it permanently encloses the radiation attenuating member, or alternatively may be configured so that the radiation attenuating member may be selectively removed. According to an alternative embodiment, drape 30 may include a radiation attenuating member that is not enclosed by a covering 46. According to another alternative embodiment, drape 30 may include a covering 46 that is integrally formed with a radiation attenuating member.

Referring still further to FIG. 1, radiation attenuation system 20 is also shown as including flap 50 and a corresponding support structure (e.g., frame, etc.), shown as a plurality of support members 60, which are used to provide rigidity to flap 50 and/or to support or move flap 50 to the extended position. According to the embodiment illustrated, flap 50 is a substantially rectangular member having a width 52 that is between approximately 6 inches and approximately 20 inches and a length 54 that is between approximately 6 inches and approximately 30 inches. According to one exemplary embodiment, flap 50 has a width 52 of approximately 11 inches and a length 54 of approximately 14 inches. According to the various exemplary embodiments, flap 50 may have any of a variety of shapes (e.g., circular, triangular, non-uniform, square, etc.) provided in any of a number of sizes.

Like drape 30, flap 50 includes one or more radiation attenuating members (e.g., sheets, films, pads, inserts, etc.) made of a radiation attenuating material. According to an exemplary embodiment, flap 50 is formed of the same radiation attenuating material forming drape 30. As such, flap 50 is generally light and flexible member capable of being bent, folded, reconfigured, etc., or otherwise manipulated. In addition, like drape 30, flap 50 may include a covering which encloses or encapsulates at least a portion of the radiation attenuating member.

Flap 50 is coupled to drape 50 and includes a first region 56 that is intended to be coupled to drape 30 and a second region 58 that is configured to be movable relative to drape 30. Flap 50 may be coupled to drape 30 using any known or otherwise suitable technique. For example, flap 50 may be coupled to drape 30 using mechanical fasteners (hook and loop fasteners, grommets, pins, snaps, clips, etc.), adhesives, welding, bonding, fusing, stitching, etc. According to an exemplary embodiment, first region of flap 50 is glued to a top or outer surface of drape 30 using a relatively permanent adhesive.

A fold line 62, spanning the width of flap 50, functionally separates first region 56 from second region 58. Fold line 62 constitutes the location on flap 50 wherein second region 58 can move relative to first region 56 and/or drape 30. Fold line 62 may be defined, at least in part, by the technique used to couple flap 50 to drape 30 (e.g., a glue seam, a stitched edge, etc.) and/or the support structure detailed below. According to the embodiment illustrated, fold line 62 is orientated to be substantially parallel to the intended path of the primary radiation beam emitted during lateral radiographic imaging of the patient. According to the various alternative embodiments, fold line 62 may extend at any orientation relative to the likely path of the primary radiation beam (e.g., 45 degrees, 90 degrees, etc.). Further, while fold line 62 is shown as a substantially continuous linear line, this line may have a curvilinear configuration, a combination of linear and curvilinear segments, or any other suitable configuration.

Flap 50 may be located at any of a number of positions relative to drape 30, but is preferably positioned where the medical personnel conducting the procedure is likely to be positioned. According to the embodiment illustrated, flap 50 is positioned near the fenestration area such that fold line 62 of flap 50 is adjacent and parallel with a lower edge of opening 40, and an outer side edge of flap 50 is adjacent and parallel to a side edge of opening 40.

According to an exemplary embodiment, flap 50 is configured to move between the first or non-extended position (shown in FIG. 1) and a second or extended position (shown in FIG. 2). Configuring flap 50 as a member that can be substantially flattened or collapsed may facilitate more efficient shipping and/or storing of radiation attenuation system 20. In the first position, flap 50 is shown as overlapping a portion of drape 30. Further, configuring flap 50 as a member that can be substantially flattened or collapsed may increase the usefulness of radiation attenuation system 20 by allowing it to be used in other radiological procedures for which is may be unnecessary or otherwise undesirable to make use of an auxiliary radiation shield extending outwardly from a primary radiation shield.

To facilitate the movement of flap 50 relative to drape 30, to support flap 50 in the extended position, and/or to otherwise provide rigidity to flap 50, one or more support members 60 are provided. Support members 60 allow flap 50 to be self-supportive. According to the embodiment illustrated, support members 60 are malleable (e.g., adjustable, flexible, impressible, pliable, etc.) members that can be configured and reconfigured with minimal effort by medical personnel so that flap 50 can be selectively arranged in a position that is desirable for the particular procedure being conducted or for the particular preferences of person conducting the procedure. Support members 60 can also be selectively reconfigured throughout the procedure to accommodate changes dictated by the procedure, the medical personnel, and/or the patient, etc. For example, it may be desirable to start a procedure with flap 50 in a position that is substantially perpendicular to drape 30 and later move (e.g., bend, shape, etc.) it to an orientation wherein flap 50 is partially collapsed so that it does not substantially interfere with the particular radiological procedure.

According to an exemplary embodiment, support members 60 are strips or bands that can be folded or bent into any of a number of positions and can then be returned to a substantially flattened positioned for storage and/or disposal of radiation attenuation system 20. The strips or bands may be formed of metal, plastic, or any other suitable material.

According to various alternative embodiments, support members 60 may be provided by a variety of know or otherwise suitable components that can support radiation attenuation system 20 in the in-use position. For example, support members 60 may be generally rigid and inflexible members which have been set in a non-adjustable in-use position. Alternatively, support members 60 may be generally rigid and inflexible members coupled to each other at one or more hinges which allow for the selective movement of flap 50 between the flattened position and the extended position. According to a further alternative embodiment, support members may be unnecessary if flap 50 (e.g., cover 42, etc.) is formed of a material that can sufficiently support radiation attenuation system 20 in the in-use position without requiring additional support.

Referring further still to FIG. 1, radiation attenuation system 20 is shown as having three support members 60 spaced apart laterally and extending in a longitudinal direction relative to drape 30 and a fourth support member 60 extending in a lateral direction relative to drape 30 and the other support members 60. The longitudinal support members 60 are shown extending between first region 56 and second region 58 of flap 50. According to an alternative embodiment, separate support members 60 may be provided for first region 56 and second region 58 and those separate support members may be coupled to each other using a suitable technique (e.g., a hinge, etc.). The lateral support member 60 may extend over all of the lateral support members 60 (as shown) or alternatively may extend only partially therebetween.

Support members 60 are shown as being provided along a back surface of flap 50, by alternatively may be sandwiched between layers of the radiation attenuating material and/or covering. Support members 60 may be coupled to each other and/or portions of flap 50 using any of a variety of known or otherwise suitable techniques including, but not limited to, mechanical fasteners (e.g., hook and loop, clips, snaps, etc.), adhesives, welding, bonding, fusing, stitching, etc.

FIG. 2 is a perspective view showing radiation attenuation system 20 in the extended position. As illustrated, flap 50 has been selectively reconfigured so that it is substantially perpendicular to at least a portion of drape 30. Such a position is obtained by manipulating (e.g., bending, shaping, etc.) support members 60 until the desired position is achieved. It should be noted that flap 50 can be supported at positions other than a substantially perpendicular position while in the extended position. Specifically, flap 50 is configured to be retained at a variety of extended or generally upright positions.

For purposes of this disclosure, the phrase "generally upright" is used broadly to define any extended position in which flap 50 may be moved to that is suitable for shielding medical personnel and/or a patient. Design criteria and application parameters may affect the definition of "generally upright." For example, "generally upright" may describe flaps that have a linear and/or a non-linear trajectories, that extend outward and/or upward in a substantially vertical direction, and/or that extend outward and/or upward at any angle ranging from approximately 0 degrees to approximately 180 degrees. Accordingly, all such definitions of "generally upright" are included in the scope of the appended claims.

Figure 4:
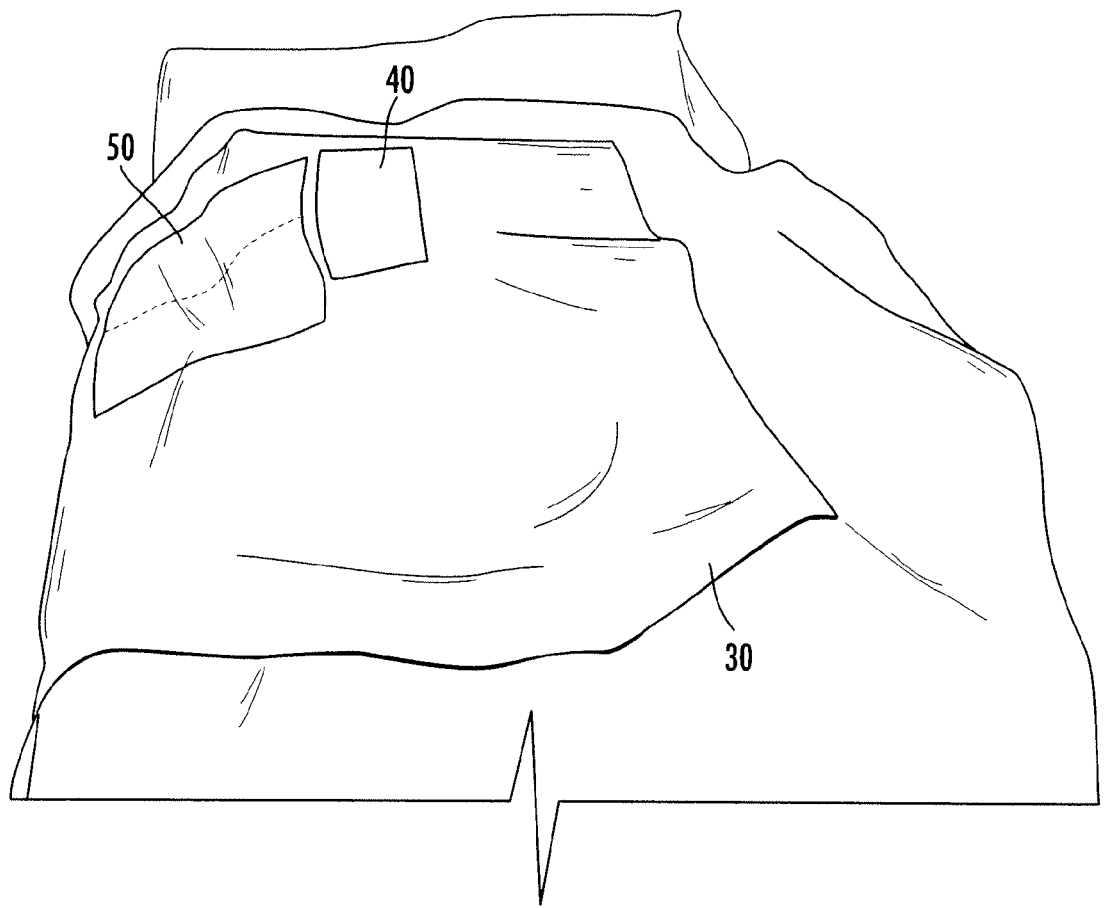
FIG. 4 is a perspective view of the radiation attenuation system of FIG. 1 applied to a patient and shown in the retracted position.
Figure 5:
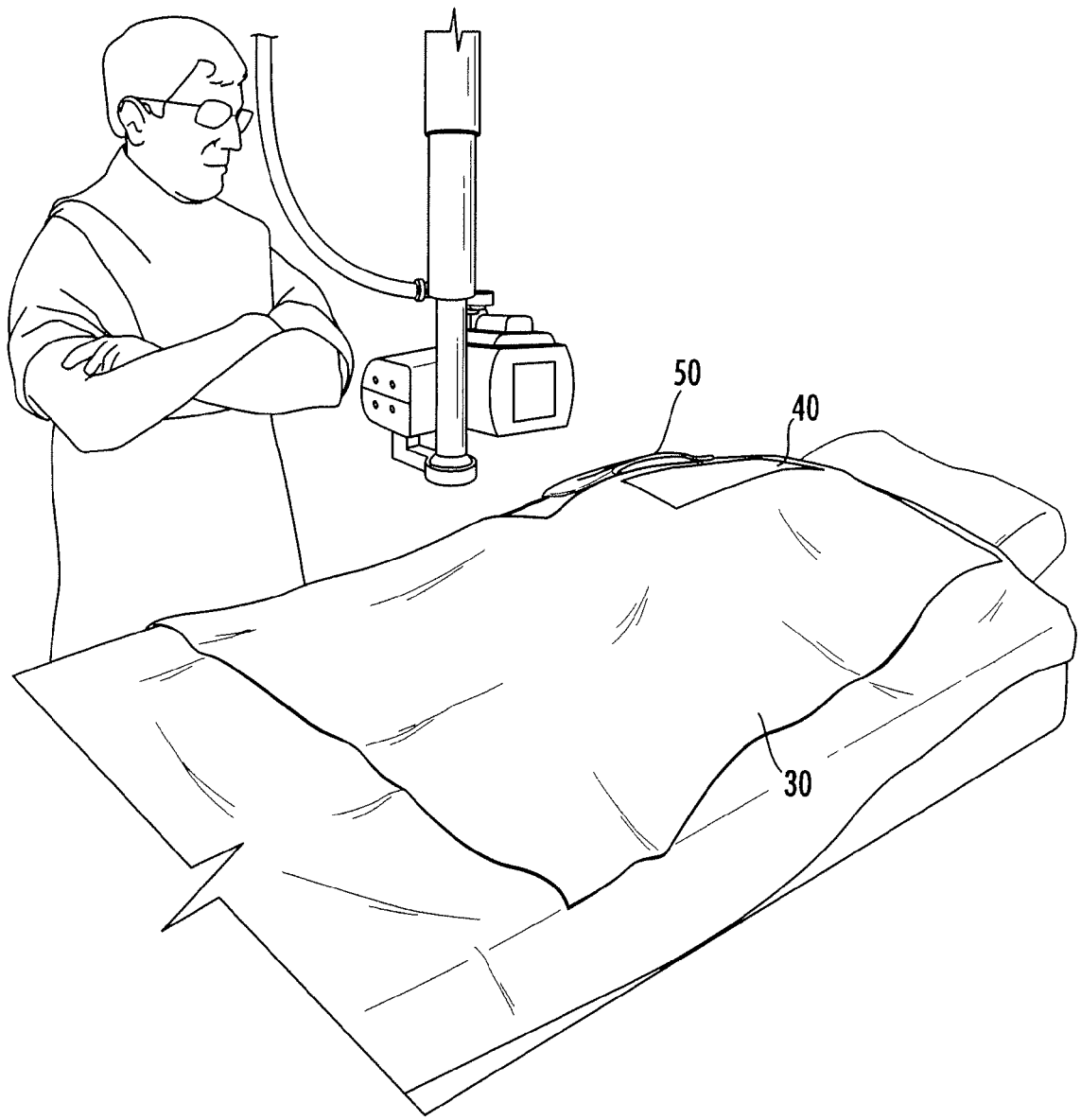
FIG. 5 is another perspective view of the radiation attenuation system of FIG. 1 applied to the patient and shown in the retracted position.

FIGS. 4 through 7 are perspective views showing radiation attenuation system 20 being used with a patient P who is positioned on a patient support structure, shown as a patient table 100. Referring to FIGS. 4 and 5 in particular, drape 30 is shown as being disposed about patient P in manner and at a position intended to reduce the amount of scatter radiation received by certain non-target areas on patient P during a radiological procedure and so that the fenestration area, specifically opening 40, is positioned over the area of interest on patient P. In these FIGURES, flap 50 is shown in a flattened positioned wherein flap 50 is collapsed onto drape 30 and lying substantially parallel thereto.

A fluoroscope is shown having a radiation emitter provided at a first lateral side of patient table 100 and a radiation receiver provided at a second lateral side of patient table 100. The fluoroscope is positioned such that it will emit a primary radiation beam in a relatively horizontal direction through patient P between the radiation emitter and the radiation receiver.

Figure 6:
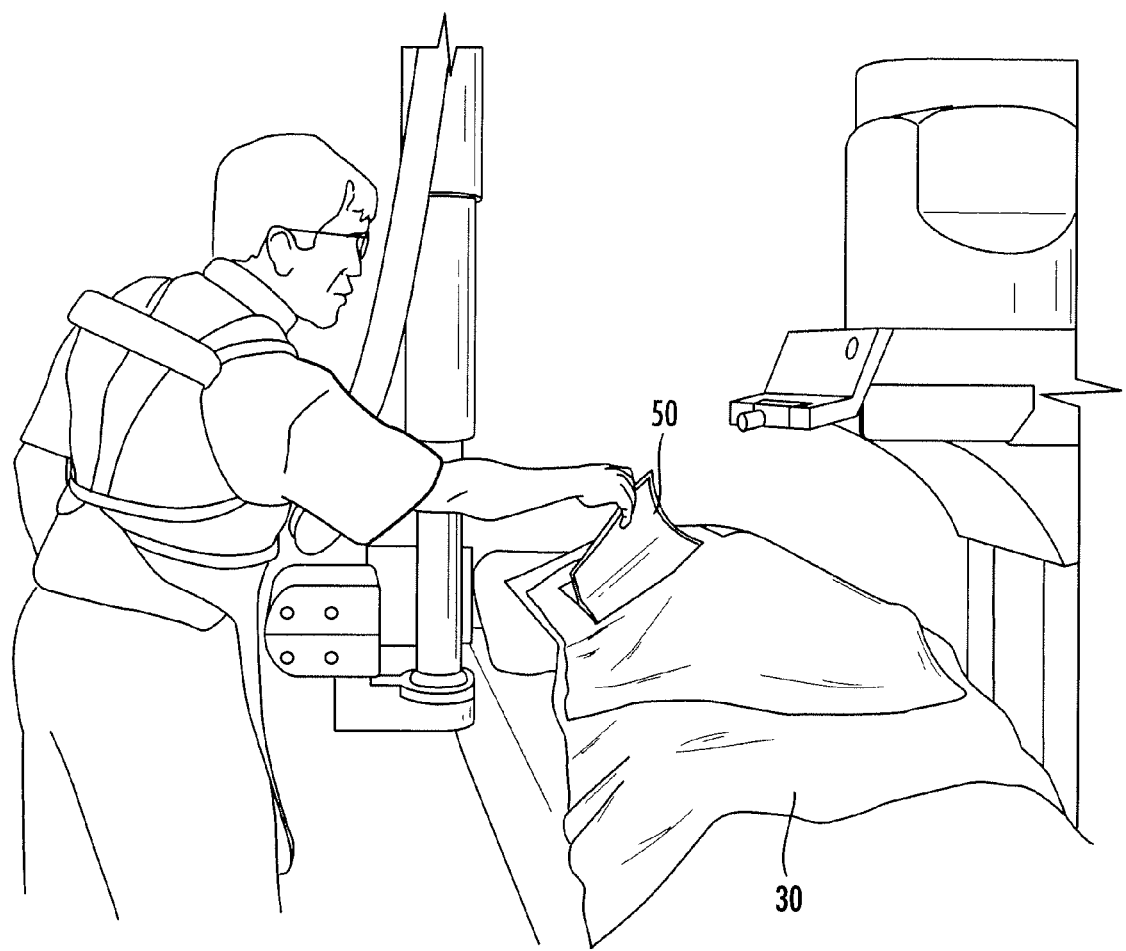
FIG. 6 is a perspective view of the radiation attenuation system of FIG. 1 applied to the patient and shown in the extended position.
Figure 7:
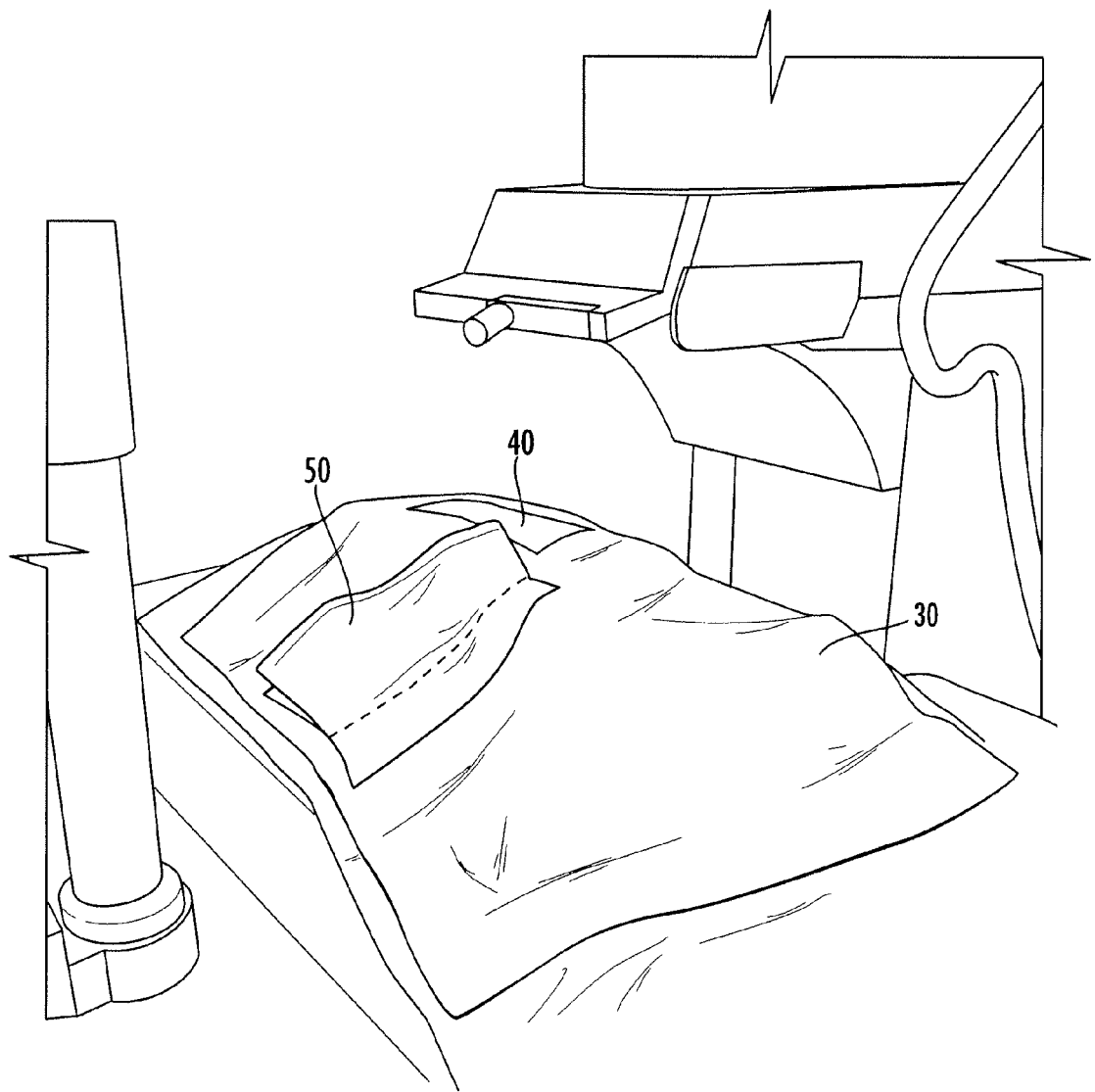
FIG. 7 is another perspective view of the radiation attenuation system of FIG. 1 applied to the patient and shown in the extended position.

Referring to next to FIGS. 6 and 7, flap 50 is shown in a generally upright position. As illustrated, flap 50 is substantially perpendicular to drape 30 and patient P. Flap 50 has been folded about fold line 62 which is positioned substantially parallel to the intended path of the primary radiation beam.

The method of using radiation attenuation system 20 is described herein with reference to FIGS. 4 through 7 and with reference to a vertebroplasty procedure. Prior to the vertebroplasty procedure a member of the medical personnel obtains radiation attenuation system 20. When first obtained, radiation attenuation system 20 is likely to have flap 50 in a relatively flattened or non-extended position. The medical personnel then places drape portion over patient P, with the side of drape 30 having flap 50 facing outward and/or upward, and aligns opening 40 so that it is over the area of interest on patient P (i.e., the target area). For the vertebroplasty procedure, wherein patient P is likely to being lying on his or her stomach, opening 40 is provided near the spine of patient P. The medical personnel then selectively moves (e.g., adjusts, reconfigures, etc.) flap 50 relative to drape 30 into a generally upright position by manipulating support members 60 until a desirable position for flap 50 is achieved. As illustrated, this position may be approximately 90 degrees relative to drape 30.

During the vertebroplasty procedure, medical personnel standing near patient P inserts a delivery device (e.g., needle, syringe, cannula, etc.) into the pedicle until it enters the vertebral body and reaches the junction of the anterior and middle thirds. Movement of the delivery device is monitored by lateral radiographic imaging provided via fluoroscopy. The primary radiation beam is applied through patient P to generate the guidance images for the medical personnel. As the primary radiation beam is applied to patient P, scatter radiation is generated due to the interaction of the primary beam with patient P, patient table 100, and/or any other object in the path of the primary radiation beam. The scatter radiation tends to be directed in all directions. Drape 30 shields certain non-target areas on patient P from this scatter radiation, while flap 50 shields medical personnel from the scatter radiation. Medical personnel assisting during the procedure may selectively adjust/reconfigure the positioning of flap 50 to provide more effective shielding and/or to prevent flap 50 from interfering with the range of movement of the medical personnel conducting the procedure. Once the delivery device is in position, a cement is prepared and injected through the delivery device and into the vertebral body. Monitoring of the cement injection is also provided via lateral radiographic imaging.

Figure 8:
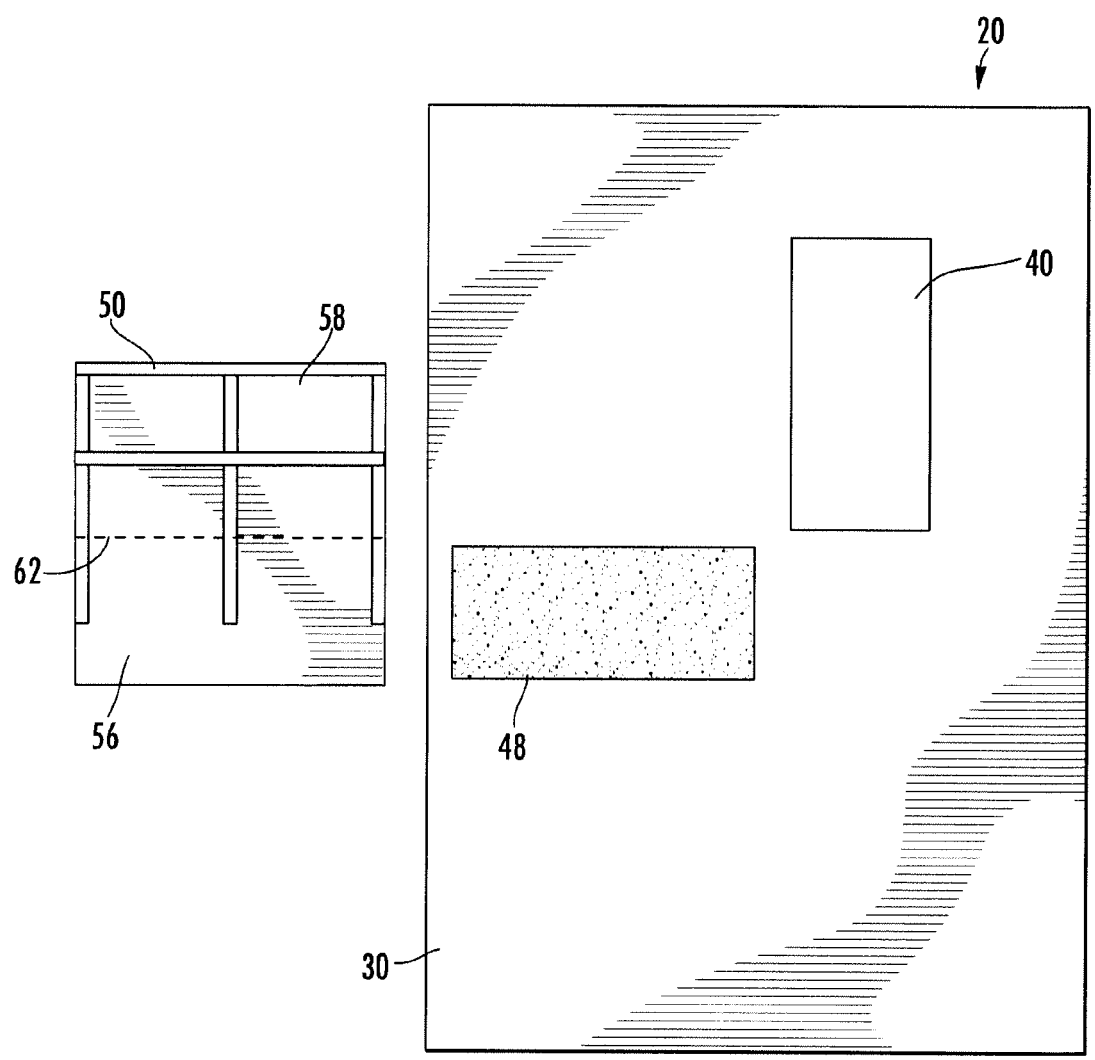
FIG. 8 is top planar view of a radiation attenuation system according to another exemplary embodiment wherein a flap is detachably coupled to a drape.

Referring next to FIG. 8, radiation attenuation system 20 is shown according to another exemplary embodiment. Radiation attenuation system 20 of FIG. 8 is similar to radiation attenuation system 20 of FIGS. 1 through 7, but is shown as including a flap 50 that is detachably coupled to drape 30. The detachable coupling of flap 50 may be provided by any of a number of techniques. According to an exemplary embodiment, a first component of a hook and loop fastener is provided along fold line 62 of flap 50 and a corresponding second component 48 of the hook and loop fastener is provided on drape 30. According to the various alternative embodiments, more than one corresponding second component may be provided about drape 30, and may be provided at more than one orientation. Such an embodiment would accommodate a variety of scenarios wherein it may be desirable to relocate flap 50 relative to drape 30.

Figure 9:
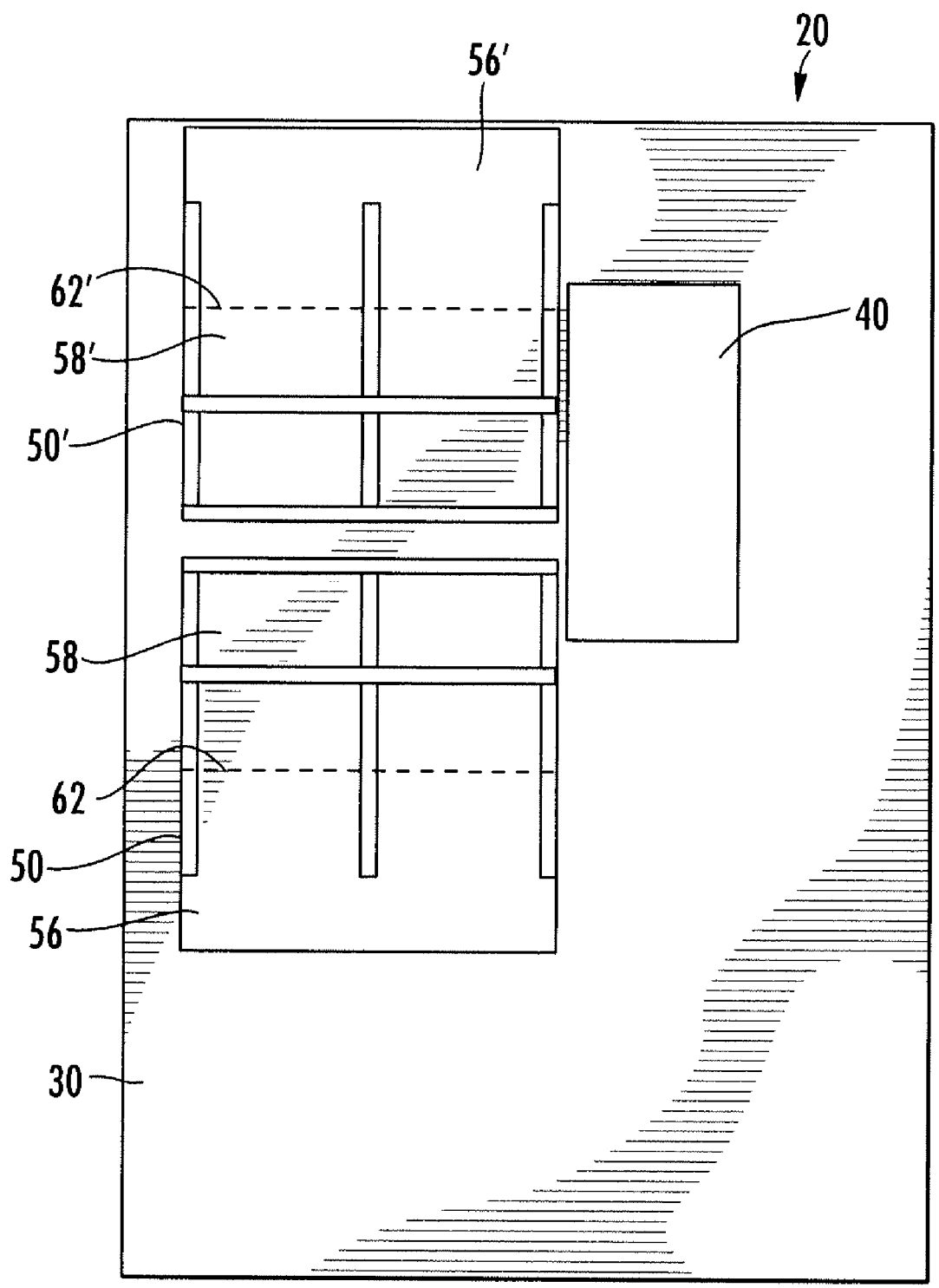
FIG. 9 is a top planar view of a radiation attenuation system according to another exemplary embodiment wherein more than one flap is coupled to a drape.

Referring to FIG. 9, radiation attenuation system 20 is shown according to another exemplary embodiment. Radiation attenuation system 20 of FIG. 9 is similar to radiation attenuation system 20 of FIGS. 1 through 7, but is shown as including a more than one flap 50. Use of multiple flaps 50 may not only provide further shielding for medical personnel, but may also provide shielding for the patient. For example, as illustrated, flap 50 is positioned as it is in the exemplary embodiment illustrated in FIGS. 1 through 7, and a second flap 50' is provided on drape 30. Second flap 50' is positioned near the top of drape 30 and may be useful for at least partially protecting the head of the patient from scatter radiation. Like flap 50, second flap 50' is intended to be manipulated and is configured to move between a generally flattened and a generally upright position.

Figure 10:
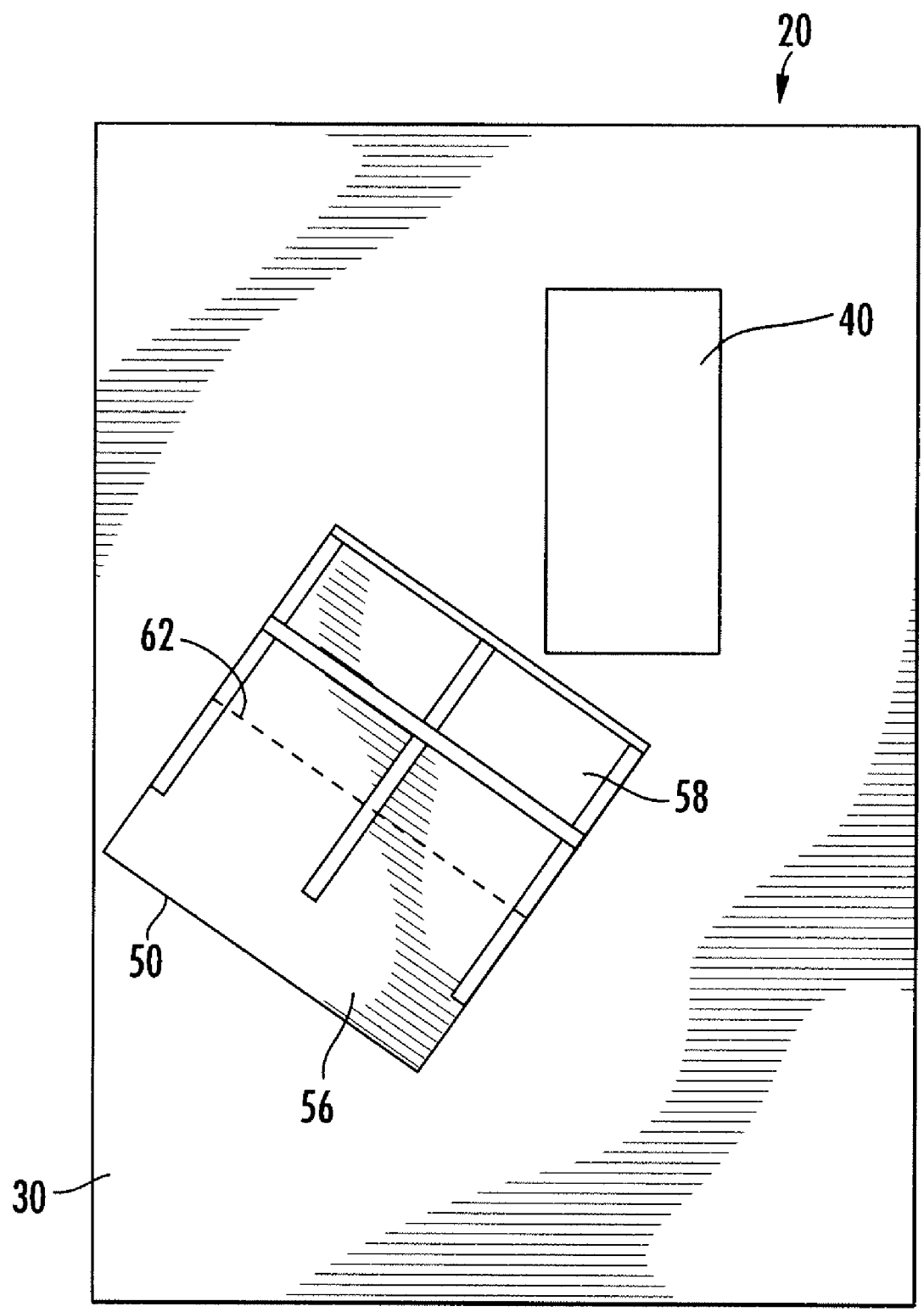
FIG. 10 is a top planar view of a radiation attenuation system according to another exemplary embodiment wherein a flap is provided at a different orientation on a drape.

Referring to FIG. 10, radiation attenuation system 20 is shown according to another exemplary embodiment. Radiation attenuation system 20 of FIG. 10 is similar to radiation attenuation system 20 of FIGS. 1 through 7, but is shown as having a flap 50 with a fold line 62 that is provided at an orientation that is likely to be angled relative to a path of a primary radiation beam during lateral imaging of a patient. For example, fold line 62 and the path of the primary radiation beam may create an angle that is between approximately 0 degrees and approximately 90 degrees, and more particularly between approximately 20 degrees and approximately 60 degrees. According to the various alternative embodiments, fold line 62 may be curvilinear or partially curvilinear.

Figure 11:
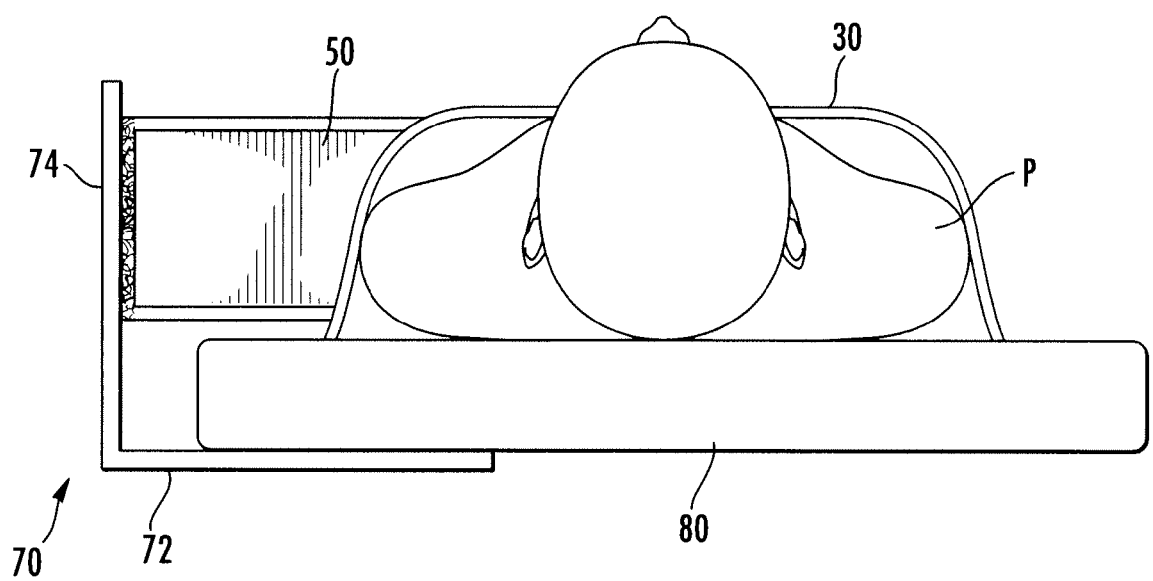
FIG. 11 is cross-sectional view of a radiation attenuation system according to another exemplary embodiment wherein a bracket is provided to support a flap.

Referring to FIG. 11, which is a cross-sectional view of a patient P, radiation attenuation system 20 is shown according to another exemplary embodiment. Radiation attenuation system 20 of FIG. 11 is similar to radiation attenuation system 20 of FIGS. 1 through 7, but utilizes a separate support frame, shown as a support bracket 70 to support flap 50 in the generally upright position. According to the embodiment illustrated, bracket 70 is a substantially rigid, L-shaped bracket having a first portion 72 (e.g., a first leg, horizontal segment, etc.) configured to be positioned under a patient cushion 80 on a patient table and a second portion 74 (e.g., second leg, vertical segment, etc.) configured to support flap 50 in the extended or open position. Bracket 70 may be selectively added to radiation attenuation system 20 when in it is desirable to utilize flap 50 in an upright position. When use of flap 50 is not required or undesirable, bracket 70 can be removed from radiation attenuation system 20 and stowed in a convenient location (e.g., cabinet, etc.).

According to the embodiment illustrated, flap 50 is provided in a generally upright position wherein flap 50 extends outward at a lateral side of the patient to shield medical personnel. To support flap 50 in the generally upright position, flap 50 is coupled to the second portion 74 of bracket 70. In order to maintain a sterile field during the radiological procedure, a cover, such as a sterile bag or wrap, can be applied to bracket 70. Flap 50 may be coupled to bracket 70, and/or to a sterile cover applied to bracket 70, using any of a variety of fastening techniques mentioned throughout this disclosure or any other suitable technique. Bracket 70 may have any of a number of shapes which allow flap 50 to be supported at any of a number of positions.

For any of the embodiments described herein, one or more of the components of radiation attenuation system 20 (e.g., drape 30, flap 50, etc.) may be generally disposable in whole or in part, thereby minimizing ancillary sources of contamination that may arise from multiple uses. According to another suitable embodiment, one or more of the components of radiation attenuation system 20 are generally non-toxic, recyclable, and/or biodegradable. According to an alternative embodiment, one or more of the components of radiation attenuation system 20 may be reusable. According to a preferred embodiment, one or more of the components of radiation attenuation system 20 may be sterilized between uses to minimize the likelihood of bacteriological or virus contamination. Sterilization may be performed in any convenient manner, including gas sterilization and irradiation sterilization.

It is important to note that the construction and arrangement of the elements of the radiation attenuation system as shown in the illustrated embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, or the length or width of the structures and/or members or connectors or other elements of the system may be varied. It should be noted that the elements and/or assemblies of the system may be constructed from any of a wide variety of materials that provide sufficient strength or durability, in any of a wide variety of colors, textures and combinations. For example, the radiation attenuation material may be a relatively flexible material, or alternatively, may be a relatively rigid material. Further, drape 30 may not include the fenestration area if drape 30 is not going to be used for invasive procedures. Further, while lateral radiographic imaging is used above with reference to a primary radiation beam that is generally parallel to a patient table, the angle at which the primary radiation beam may emitted relative to a patient table during lateral radiographic imaging may be up to approximately 45 degrees (or any other degree of obliquity) relative to the patient table. Accordingly, all such modifications are intended to be included within the scope of the present inventions. Other substitutions, modifications, changes and omissions may be made in the design, operating conditions and arrangement of the preferred and other exemplary embodiments without departing from the spirit of the present inventions.

The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating configuration and arrangement of the preferred and other exemplary embodiments without departing from the spirit of the inventions as expressed in the appended claims.

What is claimed is:

1. A radiation attenuation system for attenuating radiation during lateral radiographic imaging of an object, the system comprising:
   a first radiation attenuating barrier substantially conformable to the object and configured to at least partially cover the object, the first radiation attenuating barrier having a fenestration area defining at least one opening that provides unobstructed access to the object; and
   a second radiation attenuating barrier having a first portion and a second portion, the first portion being coupled to the first radiation attenuation barrier, the second portion being selectively movable relative to the first portion and the first radiation attenuating barrier between a collapsed position and a generally upright position, the second portion being substantially coplanar with the first portion when in the collapsed position,
   wherein the first portion is coupled to the first radiation attenuating barrier at a position offset from the at least one opening so that the second portion substantially overlaps the first radiation attenuating barrier when in the collapsed position rather than the fenestration area so that the at least one opening of the fenestration area still provides unobstructed access to the object when the second portion is in the collapsed position.

2. The system of claim 1, wherein the second radiation attenuating barrier extends at least partially across the first radiation attenuating barrier in a lateral direction.

3. The system of claim 1, wherein the first portion of the second radiation attenuating barrier is fixedly coupled to the first radiation attenuating barrier.

4. The system of claim 1, further comprising a support structure coupled between the first radiation attenuating barrier and the second radiation attenuating barrier to support the second radiation attenuating barrier in the generally upright position.

5. The system of claim 4, wherein the support structure comprises a plurality of malleable members that are adjustable to a number of positions.

6. The system of claim 1, wherein the second radiation attenuating barrier is perpendicular to the first radiation attenuating barrier when in the generally upright position.

7. The system of claim 1, wherein the second radiation attenuating barrier is rotatable about a fold line that is substantially parallel to an intended path of a primary radiation beam, the fold line separates the first portion from the second portion.

8. The system of claim 1, wherein the second radiation attenuating barrier is provided adjacent to the fenestration area.

9. The system of claim 1, wherein the second radiation attenuating barrier is supported in the generally upright position by a frame structure.

10. The system of claim 9, wherein the frame structure is removably coupled to the second radiation attenuating barrier, the frame structure being a substantially L-shaped bracket.

11. A shield for attenuating radiation during lateral radiographic imaging of a patient, the shield comprising:
- a drape formed of a first radiation attenuating material and being substantially conformable to the patient, the drape being configured to at least partially cover a non-target area on the patient, the drape having a fenestration area defining at least one opening that provides unobstructed access to the patient; and
- a flap formed of a second radiation attenuating material and coupled to the drape, the flap being selectively moveable relative to the drape between a substantially flat position and a generally upright position, the flap being configured to overlap a portion of the first radiation attenuating material when in the substantially flat position rather than the fenestration area so that the at least one opening of the fenestration area still provides unobstructed access to the patient when the flap is in the substantially flat position; and
- a support structure coupled to the flap for retaining the flap in the substantially upright position,
- wherein the flap is configured to attenuate scatter radiation during lateral radiographic imaging of the patient.

12. The shield of claim 11, wherein the flap comprises a first portion and a second portion, the first portion being coupled to the drape, the second portion being moveable relative to the first portion and the drape between the substantially flat position and the generally upright position.

13. The shield of claim 12, wherein the first radiation attenuating material and the second radiation attenuating material are the same material, the material being a relatively light weight and flexible material.

14. The shield of claim 12, wherein the flap is selectively reconfigurable to a number of different positions relative to the drape.

15. A method of attenuating radiation during lateral radiographic imaging of a patient, the method comprising:
- providing a radiographic device configured to emit a primary radiation beam at a first lateral side of the patient towards a second lateral side of the patient in a direction that is substantially perpendicular to a longitudinal axis of the patient;
- positioning a first radiation shield at least partially over a non-target area on the patient, the first radiation shield being substantially conformable to the patient;
- aligning a fenestration area of the first radiation shield with a target area on the patient to provide substantially unobstructed access to the patient; and
- moving a second radiation shield between a stowed position and a substantially upright position, the second radiation shield being offset from the fenestration area and overlapping the first radiation shield when in the stowed position rather than the fenestration area so that the fenestration area still provides unobstructed access to the patient when the second radiation shield is in the stowed position, the second radiation shield being coupled to the first radiation shield and configured to attenuate scatter radiation during lateral radiographic imaging of the patient; and
- supporting the second radiation shield in the substantially upright position in a manner so that medical personnel does not have to hold the second radiation shield.

16. The method of claim 15, further comprising positioning the second radiation shield at an orientation that is substantially perpendicular relative to the first radiation shield.

17. The method of claim 15, further comprising using a frame structure coupled to the second radiation shield to support the second radiation shield at the orientation that is substantially upright relative to the first radiation shield.

18. The method of claim 17, wherein the frame structure is configured to be selectively removed from the second radiation shield.

19. The method of claim 15, further comprising removing the second radiation attenuation shield from the first radiation attenuation shield.

20. The method of claim 19, further comprising moving the second radiation shield to a third position during lateral radiographic imaging of the patient by selectively reconfiguring the second radiation shield.

* * * * *